(12) United States Patent
Mayerhofer

(10) Patent No.: US 7,786,101 B2
(45) Date of Patent: Aug. 31, 2010

(54) CARDIOVASCULAR PROTECTION USING ANTI-ALDOSTERONIC PROGESTINS

(75) Inventor: Siegfried Mayerhofer, Vienna (AT)

(73) Assignee: Bayer Schering Pharma AG, Berlin (DE)

(*) Notice: Subject to any disclaimer, the term of this patent is extended or adjusted under 35 U.S.C. 154(b) by 1309 days.

(21) Appl. No.: 10/701,178

(22) Filed: Nov. 5, 2003

(65) Prior Publication Data
US 2005/0096303 A1 May 5, 2005

Related U.S. Application Data

(60) Provisional application No. 60/608,961, filed on Nov. 5, 2002.

(51) Int. Cl.
A61K 31/56 (2006.01)
(52) U.S. Cl. .................................................... 514/182
(58) Field of Classification Search ................. 514/182
See application file for complete search history.

(56) References Cited

U.S. PATENT DOCUMENTS

| | | | |
|---|---|---|---|
| 4,217,347 | A | 8/1980 | Horovitz et al. |
| 5,001,113 | A | 3/1991 | Williams et al. |
| 5,789,442 | A | 8/1998 | Garfield et al. |
| 5,922,349 | A | 7/1999 | Elliesen et al. |
| 6,083,528 | A | 7/2000 | Elliesen et al. |
| 6,121,465 | A | 9/2000 | Mohr et al. |
| 6,177,416 | B1 | 1/2001 | Laurent et al. |
| RE37,564 | E | 2/2002 | Spona et al. |
| 2001/0056068 | A1 | 12/2001 | Chwalisz et al. |
| 2002/0111337 | A1 | 8/2002 | Fedde et al. |
| 2002/0132801 | A1* | 9/2002 | Heil et al. .................. 514/175 |
| 2002/0136775 | A1 | 9/2002 | Thosar et al. |
| 2003/0096798 | A1 | 5/2003 | Williams et al. |
| 2004/0034001 | A1 | 2/2004 | Karara |

FOREIGN PATENT DOCUMENTS

| | | |
|---|---|---|
| WO | WO 9515166 | 6/1995 |
| WO | WO 9806738 | 2/1998 |
| WO | WO 9824801 | 6/1998 |
| WO | WO 0038725 | 7/2000 |
| WO | WO 0115701 | 3/2001 |
| WO | WO 0134132 | 5/2001 |
| WO | WO 0152857 | 7/2001 |
| WO | WO 0195892 | 12/2001 |
| WO | WO 0209683 | 2/2002 |
| WO | WO 0209759 | 2/2002 |
| WO | WO 0217895 | 3/2002 |
| WO | WO 02055086 | 7/2002 |

OTHER PUBLICATIONS

Hassager et al., Circulation, 1987, 76(4):753-758.*
Gilligan et al., Circulation, 1994;90:786-791.*
Hayslett JP: A New Role for Progesteron: An agonist for Mineralocorticoid Receptor Activation and Pregnancy-Related Hypertension. American Journal of Kidney Disease. vol. 38, No. 4 Oct. 2001: 893.5.
Quinkler M, Meyer B, Bumke-Vogt C, Grossmann C, Gruber U, Oelkers W, Diederich S, Bahr V: Agonistic and Antagonistic properties of progesterone Metabolites at the human mineralocorticoid receptor. Eur. J. Endocrinol Jun. 2002; 146(6): 798-99.
Ferrari P, Bianchetti M, Frey FJ: Juvenile hypertension, the role of genetically altered steroid metabolism. Horm. Res. 2001; 55(5); 213-23.
Coats AJ: Exiting new drugs on the horizon-eplerenone a selective aldosterone receptor antagonist (SARA). Int. J. Cardiol Aug. 2001; 80(1); 1-4.
McMahon EG: Recent studies with eplerenone, a novel selective aldosterone receptor antagonist. Curr. Opin. Pharmacol. Apr. 2001; 1(2): 190-6.
Williams ES, Miller JM: Results from late-braking clinical trial sessions at the American College of Cardiology 51s$^r$ Annual Scientific Session. J. Am. Coll. Cardiol Jul. 3, 2002; 40(1): 1-18.
Brigitte Aflao-Calderon: HRT, Women and Heart Diseases: What we need to know about prevention. http://www.medscape.com/viewarticle/ 440744.
Laurence Udoff, MD: Continuos estrogen-progestin replacement therapy in postmenopausal women. http//www.uptodate.com.
Aflalo-Calderon B. HRT, women, and heart disease: what we need to know about prevention, Medscape Cardiology 6(2), 2002.
Nelson et al. Post-menopausal hormone replacement therapy: J Am Medical Ass, Aug. 21, 2002; vol. 288, No. 7, pp. 872-891.
Delayani JA: Mineralocorticoid receptor antagonists; the evolution of utility and pharmacology. Kidney INt, Apr. 2000 57(4) 1408-1411.
Stier et al. aldosterone as a mediator in cardiovascular injury. Cardiol Rev 2002, Mar.-Apr. 10(2), 97-107.

(Continued)

*Primary Examiner*—San-ming Hui
(74) *Attorney, Agent, or Firm*—Millen, White, Zelano & Branigan, P.C.

(57) ABSTRACT

A composition comprises drospirenone as the sole therapeutically active agent.

9 Claims, No Drawings

OTHER PUBLICATIONS

Martin and Krum; Eplerenone. Current opinion in investigational drugs, 2001, 2(4), 521-525.

Hamedii and Chadow: The promise of selective aldosterone receptor antagonist for the treatment of hypertension and congestive heart failure. Curr Hypertens Rep, Aug 2, 2000(4), 378-383.

Delayani et al: Eplerenone; a selective aldosterone receptor antagonist (SARA), cardiovascular Drug Rev 2001 FAII, 19(3) 185-200.

Pitt et al; the effect of Spironolactone on morbidity and mortality in patients with severe heart failure, New Engl. J Med, vol. 341, No. 10, pp. 709717,1999.

Krattenroacher R; Drospirenone: pharmacology and pharmacokinetics of a unique progestogen. Contraception Jul. 2000, 62(1); 29-38.

Norman P, Drospirenone. Drugs of the future 2000, 25(12, 1247-1256).

Pollow et al: dihydrospiorenone, a novel synthetic progrestagen, characterisation of binding to different receptor proteins. Contraception, 1992, 46, 561-574.

Oelkers et al: Effect of an oral contraceptive containing Drospirenone in the reninangiotensin-aldosterone system in healthy female volunteers, Gynecol endocrinol 2000, 14, 204-213.

Preston et al, Additive effect of drospirenone/17β-estradiol in hypertensive postmenopausal women receiving Enalapril (Am J Hypertension, 2002, 15 (816-822).

Delyani et al: effect of a selective aldosterone receptor in myocardial infarction. Am J Physiol Heart Circ Physiol, vol. 50, H647-H654, 2001.

Wallen et al. Gender-difference in myocardial adaption to afterload in normotensive and hypertensive rats. In hypertension, 2000; 36:774-779.

Wilson at al., (1984) "A prospective controlled study of the effect on blood pressure of contraceptive preparations containing different types and dosages of progestogen" *Brit. J. Ostet Gynecol* 91, 1254-1260.

Nichols et al., (1993) "Effect of four combined oral contraceptives on blood pressure in the pill-free interval" *Contraception* 47, 367-376.

Oelkers at al., (1974) "Effects of Progesterone and Four Synthetic Progestagens on Sodium balance and the Renin-Aldosterone System in Man" *J. Olin. Endocrinol Metab* 39, 882-890,.

Rylance et al., (1985) "Natural progesterone and antihypertensive action" *Brit. Med J* 290, 13-14.

Luotola, (1983) "Blood pressure and hemodynamics in postmenopausal women during estradio1-17β substitution" *Ann Clin Res* 15 (Suppl. 38), 9.

Mashchak et al., (1985) "Estrogen replacement therapy and hypertension" *J. Reprod Mod* (Suppl 10), 805.

Rajkumar et al., (1997) "Hormonal therapy increases arterial compliance in postmenopausal woman" *J. Am Coll Cardiol* 30, 350-356.

Hayward et al., (1997) "Effect of hormone replacement therapy on non-invasive cardiovascular haemodynamics" *J Hypertens* 15, 989-993.

Mercuro et al., (1998) "Estradio1-17 beta reduces blood pressure and restores the normal amplitude of the circadlan blood pressure rhythm in postmenopausal hypertension" *Am J Hypertens* 11, 909-913.

Wren et al., (1983) "The effect of type and dose of oestrogen on the blood pressure of post-menopausal women" *Maturitas* 5, 135-142.

Seely et al., (1999) "Estradiol with or without progesterone and ambulatory blood pressure in postmenopausal woman" *Hypertension* 33, 1190-1194.

Mercuro et al., (1997) "Effects of acute administration of transdermal estrogen on postmenopausal women with systemic hypertension" *Am J. Cardiol* 80, 652-655.

The Writing Group for the PEPI Trial (1995) "Effects of estrogen of estrogen/progestin regimens on heart disease risk factors in postmenopausal women" *JAMA* 273, 199-208.

Pripp et al., (1999) "A randomized trial on effects of hormone therapy on ambulatory blood pressure and lipoprotein levels in women with coronary artery disease" *J Hypertens* 17, 1379-1386.

Manhem et al., (1998) "Transdermal oestrogen reduces daytime blood pressure in hypertensive women" *J Hum Hypertens* 12, 323-327.

van Ittersum et al., (1998) "Ambulatory-not office-blood pressures decline during hormone replacement therapy in healthy postmenopausal women" *Am J Hypertens* 11, 1147-1152.

Hayward et al., (2001) "Effect of combination hormone replacement therapy on ambulatory blood pressure and arterial stiffness in diabetic postmenopausal women" *Am J Hypertens* 14, 699-703.

Oelkers, (1995) "Effects of estrogens and progestogens on the rennin-aldosterone system and blood pressure" *Steroids* 61, 166-171.

Oelkers, (2001) "Reply to Letter to the Editor" *Gynecol Endocrinal* 14, 477-478.

Karara et al., (2001) Thirtieth Annual ACCP Meeting Abstract, Abstract #45, Effect of Drospirenone/estradiol combination product on the serum potassium of mildly hypertensive postmenopausal women maintained on enalapril maleate in *J. Clin Pharmacol.* 41, 1014-1033, p. 1024.

Epstein, (2001) "Aldosterone and the hypertensive kidney: its emerging role as a mediator of progressive renal dystunction; a paradigm shift" *J. Hypertens* 19(5), 829-841.

Duprez et al., (2000) "Aldosterone and Vascular Damage" *Curr Hypertens Reports* 2, 327-334.

Farquharson et al., (2000) "Spironolactone increases Nitric Oxide Bioactivity, Improves Endothelial Vasodilator Dysfunction, and Suppresses Vascular Angiotensin I/Angiotensin II Conversion in Patients with Chronic Heart Failure" *Circulation* 101, 594-597.

MacFadyen et al., (1997) "Aldosterone blockade reduces vascular collagen turnover improves heart rate variability and reduces early morning rise in heart rate in heart failure patients" *Cardiovasc Res* 35, 30-34.

Chrysostomou et al., (2001) "Spironolactone in addition to ACE inhibition to reduce proteinuria in patients with chronic renal disease" *N. Engl J Med* 345, 925-926.

Oelkers et al., (1995) "Effects of a New Oral Contraceptive Containing an Antimineralocorticold Progestogen, Drospirenone, on the Renin-Aldosterone System, Body Weight, Blood Pressure, Glucose Tolerance, and Lipid Metabolism" *Journal of Clinical Endocrinology and Metabolism*, vol. 80, No. 6, 1816-1821.

Fuhrmann et al., (1996) "The Novel Progestin Drospirenone and its Natural Counterpart Progesterone: Biochemical Profile and Antiandrogenic Potential" *Contraception*, 54: 243-251.

Muhn et al., (1995) "Drospirenone: a Novel Progestogen with Antimineralocorticold and Antiamdrogenic Activity" *Ann. N.Y. Acad. Sci*, 761 (Steroil Receptors and antiangrogenic activity), 311-325.

Skouby, (2000) "The rationale for a wider range of progestogens" *Climacteric*, vol, 3, (Suppl. 2); 14-20.

Oelkers et al., (1991) "Dihydrospirorenone, a New Progestogen with Antimineraloconcoid Activity: Effects on Ovulation, Electrolyte Excretion, and the Renin-Aldosterone System in Normal Women" *Journal of Clinical Endocrinology and Metabolism*, vol. 73, No. 4, 837-842.

Parsey et al., (2000) "An Open-Label, Multicenter Study to Evaluate Yasmin, a Low-Dose Combination Oral Contraceptive Containing Drosplrenone, a New Progestogen" *Contraception*, 61; 105-111.

Oelkers W., "Drospirenone—a new progestogen with antimineralocorticoid activity, resembling natural progesterone," The European Journal of Contraception & Reproductive Health Care; The Official Journal of the European Society of Contraception, England, Dec. 2000, pp. 17-24, vol. 5, suppl. 3, XP009015507, ISSN: 1362-5187.

Krause et al., "Determination of plasma levels of Spirorenone, a new aldosterone antagonist, and one of its metabolites by high-performance liquid chromatography," Journal of Chromatography, 1982, pp. 37-45, vol. 230, Biomedical Applications, Elsevier Scientific Publishing company, Amsterdam, Netherlands.

Schering AG, "Spirorenone," Drugs of the Future, 1986, pp. 478-481, vol. 10, No. 6.

Krause et al., "Isolation and Identification of Spirorenone Metabolites from the Monkey (Macaca Fascicularis)," Steroids, pp. 80-91, vol. 40, No. 1.

Merck Index, 11th Ed., 1989Monograph 3521, p. 557-558.

Berger, V. et al, "Influence Of Different Progestogens On Blood Pressure Of Non-Anaesthetized Male Spontaneously hypertensive Rats", Contraception, 46:83-97, 1992.

Karara et al., "Pharmacokinetics and Pharmacodynamics of Drospirenone-Estradiol Combination Hormone Therapy Product Coadministered With Hydrochlorothiazide in Hypertensive Postmenopausal Women", pp. 1292-1302.

Preston et al., "Randomized, placebo-controlled trial of the effects of drospirenone-estradiol on blood pressure and potassium balance in hypertensive postmenopausal women receiving hydrochlorothiazide", pp. 408-414.

Abstract—Raij et al.—Am J Hypertens (2000) 13, 29A-29A; doi:SO895-7061 (00)00389-1—"Estrogen deficiency promotes hypersensitivity to the hypertensinogenic effects of angiotensin ii (aii),".

Hypertension—Journal of the American Heart Association—"Estrogen Depletion Increases Blood Pressure and Hypothalamic Norepinephrine in Middle-Aged Spontaneously Hy7pertensive Rats", Pang et al., pp. 1-4.

Angeliq® package insert (2005).

Yasmin® package insert (2003).

Office Action dated Nov. 20, 2007 in U.S. Appl. No. 10/701,178 filed Nov. 5, 2003 (publication No. 2004/0034001).

Reply dated Aug. 20, 2008 in U.S. Appl. No. 10/701,178 filed Nov. 5, 2003 (publication No. 2004/0034001).

Office Action dated Nov. 17, 2008 for U.S. Appl. No. 10/421,940, filed Apr. 24, 2003.

Aldactone® spironolactone tablets leaflet - pp. 2-14.

\* cited by examiner

CARDIOVASCULAR PROTECTION USING ANTI-ALDOSTERONIC PROGESTINS

This application claims the benefit of the filing date of U.S. application Ser. No. 10/287,780, filed Nov. 5, 2002 now Provisional Application Ser. No. 60/608,961, filed Nov. 5, 2002.

FIELD OF INVENTION

The present invention is directed to a pharmaceutical composition comprising Drospirenone as the sole therapeutically active agent for the prevention of cardiovascular diseases in women. Furthermore, the invention relates to methods of preventing the occurrence of cardiovascular diseases in women comprising administering a drug substance with combined progestational and anti-aldosteronic activity, such as Drospirenone. Alternatively, the method comprises administering a first drug substance with progestational activity, such as progesterone and a second drug substance with selective anti-aldosteronic activity such as Eplerenone or Spironolactone. Notably, the cardiovascular disease includes heart failure, myocardial infarction and sudden cardiac death.

BACKGROUND

In women, the risk of developing hypertension and/or cardiovascular diseases increases after entering the menopause, where ovulation stops (Aflalo-Calderon B. HRT, *women, and heart disease: what we need to know about prevention, Medscape Cardiology* 6(2), 2002). It is thought that the treatment of post-menopausal women with estrogens would antagonise the risk of hypertension and/or cardiovascular diseases, such as hypertension. However, the risk of developing hypertension and/or cardiovascular diseases by the current forms of hormone replacement therapy has not yet been verified (Nelson et al. *Post-menopausal hormone replacement therapy. J Am Medical Ass*, Aug. 21, 2002, vol 288, no 7, pp 872-891).

Hypertension has for many years been thought to be the pre-dominant factor in the development of cardiovascular diseases, but it has now been questioned to what extent anti-hypertensive agents such as ACE inhibitors prevents the development of cardiovascular diseases in women. ACE inhibitors act through maintaining electrolyte homeostasis via the renin-angiotensin-aldosterone system (RAAS) such that plasma levels of the mineralocorticoid hormone, aldosterone, are reduced due to the inhibiting of the activation of mineralocorticoid receptors in the epithelia of the kidney, colon and sweat glands, whereby aldosterone promotes the retention of sodium and the excretion of potassium.

However, recently it has been shown that mineralocorticoid receptors are also present in the cardiovascular system, such as in the heart and blood vessels, as well as in the brain (Delayani JA: *Mineralocorticoid receptor antagonists; the evolution of utility and pharmacology. Kidney INt,* 2000 Apr 57(4) 1408-1411). Moreover, animal and human studies point to the fact that aldosterone plays a role in the pathogenesis of cardiovascular and renal diseases independent of the well-known mechanism involving activation of the angiotensin to angiotensin II (Stier et al, *aldosterone as a mediator in cardiovascular injury. Cardiol Rev* 2002, mar-Apr 10(2), 97-102). Thus, it is to be expected that aldosterone via its activation of the mineralocorticoid receptors in the heart, blood vessels or brain will mediate several pathophysiological actions like for example stroke, cardiac fibrosis, ventricular hypertrophy, myocardial necrosis, heart failure (congestive heart failure), sudden cardiac death and/or myocardial infarction.

Eplerenone is a steroidal drug with aldosterone receptor blocker activity. Eplerenone is reported as being effective in the treatment of aldosterone-mediated diseases such as cardiovascular diseases (Martin and Krum; *Eplerenone. Current opinion in investigational drugs,* 2001, 2(4), 521-525). Eplerenone has a selective binding to the mineralocorticoid receptor in that other steroidal receptors are not affected, such as the estrogenic and progestational receptors. Eplerenone has been shown to provide cardioprotection in both women and men (Hamedii and Chadow: *The promise of selective aldosterone receptor antagonist for the treatment of hypertension and congestive heart failure. Curr Hypertens Rep,* 2000, Aug 2(4), 378-383, Delayani et al: *Eplerenone; a selective aldosterone receptor antagonist (SARA), cardiovascular Drug Rev* 2001 FAII, 19(3) 185-200).

Another drug substance is Spironolactone (17-hydroxy-7-alpha-mercapto-3-oxo-17-alpha-pregn-4-ene-21-carboxylic acid gamma-lactone acetate), which has been shown to decrease the morbidity and mortality among patients with severe heart failure who were already receiving ACE inhibitor therapy. Thus, an additive effect was observed (Pitt et al; *the effect of Spironolactone on morbidity and mortality in patients with severe heart failure. New Engl. J Med,* vol 341, no 10, pp 709717, 1999).

Aldosterone antagonists have been used in the treatment of aldosterone mediated pathogenic effects such as hypertension and/or cardiovascular diseases in a subject that has salt sensitivity or an elevated dietary sodium intake or both by administering one or more aldosterone antagonists such as Spironolactone (WO 01/95892).

WO 02/09759 relates to the treatment of inflammation-related cardiovascular disorders such as aetherosclerosis in a subject by administering an aldosterone antagonist and a cyclooxygenase-2 inhibitor. The aldosterone antagonist being a spirolactone-type compound (Spironolactone) and an epoxy-steroidal aldosterone antagonist.

WO 01/34132 relates to the treatment, inhibiting or preventing pathogenic change resulting from vascular injury in a human subject by administering an aldosterone antagonist.

WO 95/15166 relates to the treatment with an aldosterone antagonist such as Spironolactone and epoxymexrenone for inhibiting myocardial fibrosis in that the dosage used may not disrupt a patient's normal electrolyte and water-retention balance.

Drospirenone (DRSP), a 17α-spirolactone is an analogue to Spironolactone. Drospirenone has unlike other known progestins biochemical and pharmacological profiles similar to endogenous progesterone, especially with regard to the anti-mineralocorticoid activity in the epithelia of the kidney, colon and sweat glands and the anti-androgenic activity (Krattenmacher R; Drospirenone: *pharmacology and pharmacokinetics of a unique progestogen. Contraception* 2000, July, 62(1), 29-38; Norman P, *Drospirenone. Drugs of the future* 2000, 25(12, 1247-1256). Therefore, Drospirenone is thought to mediate the natural anti-aldosterone and vasoactive properties of endogenous progesterone in women. It is known that Drospirenone binds to mineralocorticoid receptors in competition with aldosterone so as to provide a strong anti-mineralocorticoid activity. Drospirenone is about 8 times as potent as Spironolactone (Pollow et al; *dihydrospirorenone, a novel synthetic progestagen, characterisation of binding to different receptor proteins. Contraception,* 1992, 46, 561-574).

Drospirenone is known from the patent DE 19633685 and the patent application WO 98067838, both relate to a process for producing Drospirenone, 6β,7β;15β;16β-dimethylene-3-oxo-17α-preg-4-ene-21,17-carbolactone.

Plasma aldosterone levels may be affected by administering Drospirenone: In a study implying administration of Drospirenone alone or Drospirenone in combination with ethinylestradiol demonstrated that the plasma aldosterone levels increased in both groups of therapy. (Oelkers et al: *Effect of an oral contraceptive containing Drospirenone in the renin-angiotensin-aldosterone system in healthy female volunteers, Gynecol endocrinol* 2000, 14, 204-213).

Furthermore, it has been shown that Drospirenone in combination with 17β-estradiol further reduces hypertension in postmenopausal women that suffer from hypertension and is in therapy with an ACE inhibitor, Enalapril (Preston et al, *Additive effect of drospirenonell/17β-estradiol in hypertensive postmenopausal women receiving Enalapril (Am J Hypertension,* 2002, 15 (816-822).

Drospirenone is further known from its use in contraception (WO 01/15701) and for managing HRT in post-menopausal women (WO 01/52857).

SUMMARY OF THE INVENTION

It is currently considered problematic that the hormone replacement therapy used in the clinic today does not reduce the risk of hypertension and/or cardiovascular diseases in post-menopausal women. For many years it has been the theory that estrogen replacement therapy would reduce the occurrence of cardiovascular diseases in post-menopausal women. However, according to the invention, it is found that endogenous progesterone may protect a woman from developing cardiovascular diseases because of the antagonising effect of aldosterone, such as the antagonism of aldosterone on mineralocorticoid receptors in the heart, blood vessels and brain. Endogenous levels of progesterone may begin to become deficient when women enters the age of forties or in the period of peri-menopause. After entering meno-pause, the endogenous levels of progesterone are absent.

Accordingly, it has been found that Drospirenone, a drug substance with analogous progestational as well as anti-mineralocorticoid activity as progesterone, antagonises the action of aldosterone on mineralocorticoid receptors in the heart, blood vessels and brain, resulting in the potential prevention of cardiovascular diseases in women. This observation has great significance to women with the risk of developing cardiovascular diseases, such as women with deficient levels of endogenous progesterone or women with a history of cardiovascular diseases in their family. Advantageously, women can be offered cardioprotective treatment simultaneously with the treatment of symptoms and diseases associated with deficient levels of progesterone, such as irregular bleeding, abnormal bleeding, endometrioses and symptoms on peri-menopause.

Accordingly, a first aspect of the invention relates to a pharmaceutical composition for treating and preventing aldosterone-mediated diseases, such as hypertension and/or cardiovascular diseases, comprising as the sole therapeutically active agent Drospirenone, derivatives thereof or pharmaceutically acceptable salts thereof. Thus, the composition is intended for use in monotherapy, and not necessarily together with an estrogen.

A second aspect of the invention relates to therapeutic methods of preventing and treating aldosterone-mediated diseases, such as hypertension and/or cardiovascular diseases including for example heart failure, myocardial infarction and sudden cardiac death, in a woman comprising administering a drug substance with combined progestational and anti-mineralocorticoid activity to a woman in need thereof. Typically, the woman in need thereof may be any woman with the desire of being protected from hypertension and/or cardiovascular diseases. For example, the woman may be in risk of developing cardiovascular diseases or susceptible to cardiovascular diseases, such as a hypertensive woman. Typically, the woman may have a known history of hypertension and/or cardiovascular diseases in the family, the woman may have an age of above 40, the woman may have deficient endogenous levels of progesterone, the woman may be in the peri-menopause, the menopause or the post-menopause. The therapeutic methods and medicaments of the invention also encompass the preventing and treating of aldosterone-mediated diseases, such as hypertension and/or cardiovascular diseases in a woman simultaneously with the prevention and/or treatment of diseases associated with deficient endogenous levels of progesterone. The therapeutic methods and uses of the invention are primarily directed to monotherapy with a drug substance with combined progestational and anti-mineralocorticoid activity. In a further embodiment of the invention, the combined progestational and anti-mineralocorticoid activity is achieved by combining a first drug substance with selective aldosterone antagonism (anti-mineralocorticoid activity) and substantially none or low progestational activity and a second drug substance with substantially none anti-mineralocorticoid activity but with progestational activity. In one embodiment thereof, Eplerenone and/or Spironolactone is the first drug substance with the selective aldosterone antagonism and the second drug substance is selected from conventional progestins that have none or low anti-mineralocorticoid activity.

Still further aspects of the invention relate to drug formulations comprising the combination of a first drug substance with selective aldosterone antagonist activity (anti-mineralocorticoid activity) and a second drug substance of a progestin with none or low anti-mineralocorticoid activity for the treatment and/or prevention of aldosterone-mediated diseases, such as hypertension and/or cardiovascular diseases.

In preferred embodiments of the invention, the drug substance with combined progestational and anti-mineralocorticoid activity is Drospirenone.

DETAILED DESCRIPTION

As stated, the invention lies in part in the hitherto unknown cardioprotective effect in women when being in therapy with Drospirenone. Drospirenone is a drug substance having aldosterone antagonising activity due to binding to mineralocorticoid receptors in competition with aldosterone. However, Drospirenone does also have progestational activity. Accordingly, other drug substances with equivalent pharmacological and biochemical profiles to Drospirenone, such as drug substances with combined progestational and anti-mineralocorticoid activity, are considered effective in providing cardioprotective effect. It is thought that the cardioprotective effect results from the anti-aldosterone activity of Drospirenone on mineralocorticoid receptors in the heart, the vascular system and brain. Therefore, the general concept of the invention relates to therapeutic methods and preparation of medicaments for the prevention and/or treatment of aldosterone-mediated diseases, such as hypertension and/or cardiovascular diseases, comprising administering a drug substance with combined progestational and anti-mineralocorticoid activity, or a first drug substance mainly possessing anti-mineralocorticoid activity in combination with a second drug substance mainly possessing progestational activity.

As used herein, the following phrases and terms are defined:

The term, "aldosterone-mediated diseases" encompasses diseases resulting from the activation of aldosterone receptors (mineralocorticoid receptor) by aldosterone. This activation has been shown to be a key step in the chain of events leading to a number of diseases originating in the tissue where such receptors are found. Thus, aldosterone-mediated diseases may be mediated in whole or in part, by aldosterone present in the brain, heart and blood vessels.

Typical examples on aldosterone-mediated diseases are cardiovascular diseases; renal dysfunction; liver diseases; cerebrovascular diseases; vascular diseases; retinopathy; neuropathy; insulinopathy; edema; endothelial dysfunction; baroreceptor dysfunction and migraine headaches. Hypertension is also an aldosterone-mediated disease, but it is a disease that are thought to be, at least in part, mediated by mineralocorticoid receptors in the kidney and not to the direct activation of aldosterone receptors in the heart or brain.

The aldosterone-mediated diseases may also relate to renal dysfunction such as glomerulosclerosis; end-stage renal disease; diabetic nephropathy; reduced renal blood flow; increased glomerular filtration fraction; proteinuria, decreased glomerual filtration fraction; decreased creatinine clearance; microalbuminuria; renal arteriopathy; iscemetic lesions; thrombotic lesions; global fribinoid necrosis; focal thrombosis of glomerual capillaries; swelling and proliferation of intracapillary and/or extracapillary cells; expansion of reticulated mesangial matrix with or without significant hypercellularity; and/or malignant nephrosclerosis. Furthermore, liver diseases may be mediated through aldosterone activation of mineralocorticoid receptors. Such liver diseases may be liver cirrhosis, liver ascites or hepatic congestion. In a particular embodiment, the aldosterone-mediated diseases relate to cerebrovascular disease including stroke. In further interesting embodiments, the uses and therapeutic actions of the present invention implies treating of vascular diseases such as thrombotic vascular disease; proliferative arteriopathy; atherosclerosis; decreased vascular compliance; and/or endothelial dysfunction.

In current interesting embodiments of the invention, the aldosterone-mediated disease is hypertension and/or cardiovascular disease.

In the context of the present invention, the term "cardiovascular disease" is denoted to mean a disease in the cardiovascular system that may be mediated, at least in part, by aldosterone activity on aldosterone receptors in the heart, blood vessels and/or brain, preferably the heart. Specifically, the term "cardiovascular diseases" is meant to include the following diseases and symptoms but are not limited to, heart failure; congestive heart failure; arrhythmia; diastolic dysfunction; left ventricular diastolic dysfunction; diastolic heart failure; impaired diastolic filling; systolic dysfunction; ischemia; hypertropic cardiomyopathy; sudden cardiac death; myocardial and vascular fibrosis; impaired arterial compliance; myocardial necrotic lesions; vascular damage; myocardial infarction; left ventricular hypertropy; decreased ejection fraction; cardiac lesions; vascular wall hypertrophy; endothelial thickening; and fibrinoid necrosis of coronary arteries. In some embodiments the cardiovascular disease may be ischaemic heart disease, angina pectoris, coronary heart disease, stroke, cerebrovascular disease, aortic aneurysm, peripheral arterial disease and retinal arterial disease. In interesting embodiments of the invention, cardiovascular diseases are selected from heart failure, myocardial fibrosis, sudden cardiac death and/or myocardial infarction. It should be noted that aldosterone receptors are also present in the epithelia of the kidney, colon and sweat glands for which reason aldosterone antagonist have been regarded as drug substances with some anti-hypertensive effect due to their regulation of sodium and potassium in the kidneys. Therefore, in the context of the present invention, the term "cardiovascular diseases" does not include hypertension, which is more recognised as a symptom on a cardiovascular event.

In the context of the present invention, cardiovascular diseases may not relate to inflammation-related cardiovascular disorders such as aetherosclerosis and the woman may not need to be in concurrent therapy with ACE-inhibitors, cyclooxygenase-2 inhibitors and/or β-blockers. Of importance is also that the dosage used of the drug substance exhibiting anti-mineralocorticoid and progestational effect may not disrupt a patients normal electrolyte and water-retention balance.

The term "preventing" includes either prevention of the onset of a clinical manifestation of a symptom, disease or disorder altogether or preventing the onset of a preclinically evident stage of a disease or disorder in a woman. For example, the prevention of cardiovascular diseases in a woman may be determined on the basis on the reduction of incidences in heart failure, myocardial fibrosis, sudden cardiac death and/or myocardial infarction in a population of women receiving medication with drug substances of the present invention, such as Drospirenone, for a pre-determined period of time, such as during 1, 2, 3, 4, or 5 years, in comparison to a placebo population of women not receiving medication with such drug substances. The prevention of hypertension may be determined as the reduction in diastolic and/or systolic blood pressure.

The preventive effect on cardiovascular diseases of a drug substance with anti-mineralocorticoid and progestational activity may be investigated in human or animal studies by methods known to the person skilled in the art. In human studies the end-point for determining prevention of cardiovascular diseases may for example be based on the incidences of stroke, incidences of myocardial infarct, incidences of congestive heart failure, incidences of vascular or myocardial fibrosis and/or incidences of sudden cardiac death during long-term studies in a placebo-controlled study or a comparison study involving progestins with substantially no anti-mineralocorticoid effect as the control medication. Optionally, the medication may include concurrent therapy with estrogens in that estrogens are not considered as relevant for the preventive effect on cardiovascular diseases. The reduction in the risk of hypertension, congestive heart failure, myocardial and vascular fibrosis, myocardial infarction and sudden cardiac death is of particular interest to the invention. Indications of cardiovascular diseases may be observed by a physician and through the result of laboratory analyses, such as blood gas analyses or abnormal blood parameters.

Preferably the therapeutic methods and uses of the present invention reduces the risk of hypertension and/or cardiovascular disease by at least 50%, such as at least 60, 70, 80 or 90%.

A number of animal models for the investigation of the hypertension and/or cardiovascular effect of a therapeutically active agent are available. Experiments can be carried out in rodents that are made hypertensive using surgical alterations, or in spontaneously hypertensive rodent treated with a stroke-prone substance.

For example, arterial hypertension can be induced in rodents using different techniques:

a) renovascular hypertension induced by surgically placing a constricting band around the right renal artery, to induce unilateral renal ischemia.

b) infrarenal banding to mechanically constrict blood flow through the aorta below the junction where the renal arteries branch off. (elevated blood pressure in the kidneys).
c) aldosterone infused directly into the rodents at a fixed rate via an implanted pump.

The spontaneously hypertensive rodents of the stroke-prone substrate is characterised by an increased development of severe hypertension, cerebrovascular lesions, and malignant nephrosclerosis.

During the treatment period, the rodents are monitored for hypertension, and plasma aldosterone, systolic and diastolic blood pressure, left ventricular and diastolic pressure, left ventricular dP/dt, body weight, and heart rate.

At the end of the treatment period, the rodents are sacrificed and compared between the different groups of treated with either an active agent or placebo, by examination of the heart, microscopic evaluation of the cerebrovascular damages and/or histopathologic analysis of the kidneys.

For example, the effect on a drug substance on cardiovascular injury may be investigated using L-NAME/Ang II/NaCl Hypertensive rats (Delayani et al; *eplerenone, a selective aldosterone receptor antagonist. Cardiovascular Drug Reviews* vol, 19, No 3, p 185-200).

Another animal model for testing the effect of agents on cardiovascular diseases is described in Wallen et al. Gender-differences in myocardial adaptation to afterload in normotensive and hypertensive rats. In hypertension, 2000; 36:774-779.

The mineralocorticoid receptor binding in vivo of a drug substance may be investigated in adrenolectomized rats by measuring radiolabelled aldosterone bound to receptors in the kidney, heart, blood vessels, brain or other organs in the presence of the agent (Delayani et al; *eplerenone, a selective aldosterone receptor antagonist. Cardiovascular Drug Reviews* vol, 19, No 3, p 185-200).

Other models of investigating hypertension and/or cardiovascular effects are mentioned in Delyani et al; *effect of a selective aldosterone receptor antagonist in myocardial infarction. Am J Physiol Heart Circ Physiol*, vol 50, H647-H654, 2001.

The phrase "a drug substance having progestational and anti-mineralocorticoid activity" is intended to denote a drug substance having a binding affinity to the mineralocorticoid receptor and the progesterone receptor in the order of the binding affinity observed for Drospirenone in similar doses. Thus, it is to be understood that a drug substance having a progestational and anti-mineralocorticoid effect similar to Drospirenone is characterised by having a binding affinity to the progesterone receptor and to the mineralocorticoid receptor relatively to that of Drospirenone in the range from about 50% to 150% when tested in similar doses. In some embodiments, the binding affinity relatively to Drospirenone is from about 75% to 125%, more preferably in the range of from about 85% to 115%.

The term "aldosterone antagonist" is denoted to include any substance that reduces the activity of aldosterone as a result of inhibiting its binding to the anti-mineralocorticoid receptor. It does not include substances, which reduce the amount of aldosterone synthesized or secreted by the adrenal cortex. Mespirenone is an example of an inhibitor of aldosterone synthesis.

The phrase "selective aldosterone antagonist" denotes a compound that has a binding affinity to the anti-mineralocorticoid receptor and the progestational receptor in the order of that of Eplerenone. A compound is characterised as having a selective aldosterone antagonism when the binding affinity of the compound relatively to Eplerenone with regard to the progestational receptor and the mineralocorticoid receptor is in the range of 50% to 150%, preferably in the range of 75% to 125%, more preferably in the range of 85% to 115% when tested in similar doses.

The phrase "progestin with low anti-mineralocorticoid effect" qualifies to a progestin that has a binding affinity to the mineralocorticoid receptor relatively to that of Drospirenone of no more than 10%, preferably of no more than 5% such as no more than 2%.

The phrase "progestin with substantially none anti-mineralocorticoid effect" qualifies to a progestin that has a binding affinity to the mineralocorticoid receptor relatively to that of Drospirenone of no more than 1%, preferably of no more than 0.2% such as no more than 0.01%.

A compound is characterised as having low anti-mineralocorticoid activity when the binding affinity to the relevant receptors of the test agent relatively to Drospirenone is less than 10%, preferably less than 5% such as less than 2% when tested in similar doses.

A compound is characterised as having substantially none anti-mineralocorticoid activity when the binding affinity to the relevant receptors of the compound relatively to Drospirenone is less than 1%, preferably less than 0.2% such as less than 0.01% when tested in similar doses.

The phrase "binding affinity to the progestational receptor relatively to that of Drospirenone" is characterised by the binding affinity of a test agent relatively to that of Drospirenone as determined in cytosol fractions containing expression vector for a animal or human progestational receptor, respectively. The assay can be carried out incubating the cytosols with an appropriate radiolabeled reference substances, for which the relative binding affinity value is set at 100% and the steroid competitor, as described in K. Pollow et al. *Contraception*, 46:561-574, 1992. In the event where the test agent is tested for selective aldosterone receptor antagonism, the relative binding affinity is determined relatively to Eplerenone.

The term "binding affinity to the mineralocorticoid receptor relatively to that of Drospirenone" is characterised by the binding affinity of a test agent relatively to that of Drospirenone as determined on the basis of similar doses of the two agents in cytosol fractions containing expression vector for a animal or human mineralocorticoid receptor, respectively. The assay can be carried out incubating the cytosols with an appropriate radiolabeled reference substances, for which the relative binding affinity value is set at 100% and the steroid competitor, as described in K. Pollow et al. *Contraception*, 46:561-574, 1992. In the event where the test agent is tested for selective aldosterone receptor antagonism, the relative binding affinity is determined relatively to Eplerenone.

A first aspect of the invention relates to a composition comprising as the sole therapeutically active agent Drospirenone, derivatives thereof or pharmaceutically acceptable salts thereof and one or more pharmaceutically acceptable excipient(s) or carrier(s). The term "Drospirenone" is intended to include any geometric isomer of Drospirenone, metabolites of Drospirenone and/or derivatives of Drospirenone as long as the derivatives, metabolites and salts exhibit the same or nearly the same pharmacological and biochemical activity as Drospirenone itself. That is to say that isomers, metabolites or derivatives of Drospirenone may have a progestational and anti-mineralocorticoid effect similar to that of Drospirenone. For example the binding affinity of the isomer, metabolite derivative or salt with respect to the progestational receptor and the mineralocorticoid receptor may relatively to that of Drospirenone be in the range of 50% to 150%, preferably in the range of 75% to 125%. The term "derivatives thereof" is intended to encompass esters, ethers, pro-drugs, metabolites or salts of Drospirenone, for example in the form of an oxyiminopregnane carbolactone as disclosed in WO 98/24801.

As stated, Drospirenone may be the only therapeutically active agent included in the composition. In the present context, the term "sole therapeutically active agent" is denoted to mean that substantially no other drug substances is included in the composition. However, some drug substances can be allowed as long as they are not regarded as therapeutically relevant for the treatment of hypertension and/or cardiovascular diseases or are present in a dose insufficient to prevent or treat hypertension and/or cardiovascular diseases. Moreover, other hormonal agents such as estrogens are excluded from the composition.

The composition is intended for being administered by a woman so as to prevent the development of aldosterone-mediated diseases in general and in particularly to prevent the development of hypertension and/or cardiovascular diseases. Thus, in one embodiment, the composition is in unit dosage form for the daily delivery of Drospirenone in a therapeutically effective dose for preventing hypertension and/or cardiovascular diseases in a woman. That is to say that the composition comprises a so-called cardioprotective dose. The dose may vary according to a number of factors. However, the daily delivery of Drospirenone may in general include a dose from about 0.02 mg to 5 mg. In some instances the suitable dose is from about 0.1 to 5 mg, more preferably of from about 0.2 mg to 3 mg. In particular, any suitable dose may be 0.2, 0.25, 0.5, 1, 1.5, 2, 2.5, 3, 3.5, 4, 4.5 or 5 mg dependent on the woman and the intention of preventing or treating hypertension and/or cardiovascular diseases concurrent with treating symptoms of deficient levels of progesterone, peri-menopause or post-menopause or not.

A second aspect of the invention relates to therapeutic methods or the preparation of medicaments for preventing and/or treating aldosterone-mediated diseases, such as hypertension and/or cardiovascular diseases in a woman comprising administering or preparing a medicament of a drug substance having combined progestational and anti-mineralocorticoid activity.

Alternatively, the dual progestational and anti-mineralocorticoid activity may be accomplished by providing said activity in the form of a first drug substance having anti-mineralocorticoid activity and a second drug substance having progestational activity but substantially none anti-mineralocorticoid activity. Therefore, in a third aspect the invention relates to therapeutic methods or the preparation of medicaments for preventing and/or treating aldosterone-mediated diseases, such as hypertension and/or cardiovascular diseases in a woman comprising administering or preparing a medicament of a first drug substance of a selective aldosterone antagonist and a second drug substance of a progestin with low or substantially no anti-mineralocorticoid activity.

Unlike earlier publications, it is found that prevention of hypertension and/or cardiovascular events in a woman can sufficiently be achieved upon administering the drug substance having progestational and anti-mineralocorticoid activity as the sole therapeutically active agent. That is to say that co-administering of Drospirenone with anti-hypertensive drugs or estrogens is not critical for achieving sufficient prevention of hypertension and/or cardiovascular diseases in a woman. Thus, in one preferred embodiment of the invention, the drug substance having progestational and anti-mineralocorticoid activity is the sole therapeutically active agent administered or included in a medicament. Accordingly, in another embodiment of the invention the first and second drug substances are the only two therapeutically active agents administered or included in a medicament. For example in one embodiment co-administering of an estrogen is excluded or an estrogen is excluded from the medicament. However, it should not be the understanding that a further drug substance cannot be administered or included in a medicament. For example, anti-hypertensive drugs. That is to say that in one embodiment, the methods and uses of the invention include con-current therapy with an anti-hypertensive drug.

Interestingly, the therapeutic methods of the invention may in some embodiments include the prevention and/or treatment of aldosterone-mediated diseases, such as hypertension and/or cardiovascular diseases simultaneously with the prevention and/or treatment of symptoms, diseases or disorders associated with deficient endogenous levels of progesterone in a woman.

The phrase "deficient endogenous levels of progesterone" is intended to mean that the plasma concentration of progesterone in a woman has for at least one month, as determined on a daily basis, been lower than the concentration range expected to be present during luteal phase of the menstrual cycle. The expected progesterone plasma concentration during luteal phase is in the range between 30 and 110 nmol/l. In the event where the woman is pregnant, the phrase "deficient endogenous levels of progesterone" is intended to mean progesterone plasma concentrations lower than 200 nmol to 300 nmol. The plasma concentrations of progesterone in a pregnant woman steadily rise until they peak at the end of the third trimester in the range of 320-700 nmol/l.

Deficient endogenous levels of progesterone may be found in a woman for a number of reasons. Mainly, deficient endogenous levels of progesterone are associated with irregular bleeding, abnormal bleeding, lack of ovulation, peri-menopause or post-menopause. Also a pregnant woman may suffer from deficient endogenous levels of progesterone in that high levels of progesterone are normally required in order to avoid risk of miscarriage. Furthermore, deficient endogenous levels of progesterone are characteristic for endometrioses and other gynaecological disorders.

As used herein, the term "irregular bleeding" characterises any uterine bleeding, outside the regular monthly menstrual periods of non-pregnant women. Uterine bleeding are irregular if menstrual cycles or menstrual periods are too short, too long, too frequent, too infrequent, or occur at irregular intervals which falls outside the regular 26-30 days menstrual cycle. The menstrual period is classified as too long when being delayed with 15 to 50 days or more to the expected onset of said bleeding.

The term "abnormal bleeding" characterises heavy bleeding typically soaking through enough sanitary protection products to require changing more than every one or two hours, having a period that lasts over seven days. Abnormal bleeding does not include bleeding in women who have already reached menopause, abnormal uterine bleeding due to side effects of estrogen replacement therapy, abnormal bleeding as a symptom of uterine cancer, as a result of a consequence of abnormal blood clotting normally, an inherited bleeding disorder or because of a medical illness that affects levels of blood platelets.

The term "lack of ovulation" relates to the condition in a woman, where the woman has stopped ovulating. The condition is characterised by a relative blood level of luteinizing hormone greater than 30 IU/L in a peri-menopausal/menopausal woman, in comparison with a menstruating woman with a level of 5-22 IU/L or 30-250 IU/L in respectively the follicular or luteal phase or midcycle phase.

The phrase "a woman in need of progesterone replacement therapy" qualifies a woman that is deficient in endogenous levels of progesterone, a woman that is pregnant and in risk of miscarriage and a woman that experience irregular bleeding and/or abnormal bleeding.

Therefore, in some embodiments of the invention, the therapeutic methods or medicaments are for the treatment and/or prevention of irregular bleeding; abnormal bleeding; lack of ovulation; symptoms and diseases associated with peri-menopause and/or post-menopause; risk of miscarriage; endometrioses and/or other gynaecological disorders simultaneous with the prevention of aldosterone-mediated diseases, such as cardiovascular diseases.

According to the present invention, the drug substance having progestational and anti-mineralocorticoid activity may be a steroidal compound, for example a non-epoxy spironolactone-type steroidal compound.

The term "steroidal" denotes a nucleus provided by a cyclopenteno-phenathrene moiety, having the conventional four ring members. The phrase "non-epoxy-steroidal aldosterone receptor antagonist" is intended to denote one or more drug substances characterised by a steroid-type nucleolus and with no epoxy moiety attached to the nucleolus and which binds to the aldosterone receptor as a competitive inhibitor of the action of aldosterone itself at the receptor site, so as to modulate the receptor-mediated activity of aldosterone. Drospirenone and Spironolactone is typical examples on such drug substances. As used herein "Spironolactone" refers to a molecule comprising a lactone structure coupled via a spiro configuration to a steroid structure or steroid derivative.

The non-epoxy spironolactone-type steroidal compound may further be characterised by having a relative binding affinity to the mineralocorticoid receptor and the progestational receptor of substantially the same order as drospirenone.

The progestational activity of spironolactone is far lower than that of Drospirenone within the same dosage range and the progestational effective dosage of spironolactone may disrupt a patient's normal electrolyte and water-retention balance. Therefore, it is found advantageous to use Drospirenone in preference to Spironolactone. Furthermore, some dosages of Drospirenone may antagonise aldosterone-mediated diseases without affecting the progestational activity.

In current preferred embodiments of the invention, the drug substance having progestational and anti-mineralocorticoid activity is Drospirenone.

As stated earlier, the combined progestational and anti-mineralocorticoid activity according to the invention may result from the combination of a selective aldosterone antagonist and a progestin with low or substantially none anti-mineralocorticoid activity.

In some embodiments, the selective aldosterone antagonist is a steroidal compound such as an epoxy spironolactone-type steroidal compound. The phrase "epoxy-steroidal aldosterone receptor antagonist" is intended to denote one or more drug substances characterised by a steroid-type nucleolus and an epoxy moiety attached to the nucleolus and which agent or compound binds to the aldosterone receptor as a competitive inhibitor of the action of aldosterone itself at the receptor site, so as to modulate the receptor-mediated activity of aldosterone. Eplerenone is an example of an epoxy-steroidal aldosterone receptor antagonist. The term "epoxy-steroidal" is intended to embrace a steroidal nucleus having one or a plurality of epoxy-type moieties attached thereto.

In current interesting embodiments of the invention, the selective aldosterone antagonist is Eplerenone (epoxymexrenone) or Canrenoate.

A great number of progestins with substantially no or low anti-mineralocorticoid effect are known. Examples are, but not limited to norethisterone; norethisterone acetate; levonorgestrel; gestodene; norgestilmate; dienogest; medroxyprogesterone acetate; megestrol acetate; chlormadinone acetate; or cyproterone acetate. The progestins may be in the form of its derivatives such as esters, ethers or salts, preferably esters. Progesterone may have a lower anti-mineralocorticoid effect than drospirenone and Eplerenone, in particular at those doses that are clinically relevant for exhibiting progestational effect. For that reason progesterone or a derivative thereof such as an ester or salt may also be a suitable progestin for use.

The therapeutic methods or medicaments of the invention are directed to women having the need or desire of being protected from hypertension and/or cardiovascular diseases. In general, the therapy and medicaments of the invention are directed to a woman above a specified age for reducing the risk of hypertension and/or cardiovascular disease. Therefore, in some preferable embodiments, the therapeutic methods and uses is applied to a woman above a critical age, for example a woman who may have no clinical symptoms of hypertension and/or cardiovascular disease, the only criterion being that she is above a critical age. The critical age will vary from population to population according to the incidence of cardiovascular disease or according to other factors such as diet or smoking. The critical age can be determined simply by determining the age above which 80%, such as 85%, 90% or 95% of the deaths from heart failure or cardiac infarct occur. Typically the characteristic age is above 35, such as above 40, 45 and 47, and may range from about the age from about 40 to 65.

In some embodiments of the invention, the uses and therapeutic methods of the invention is intended to healthy women irrespective of their age, e.g. women with a systolic blood pressure less than 140 mm Hg such as less than 130 mm Hg or 120 mm Hg or a diastolic blood pressure less than 105 mm Hg, such as less than 95 mm Hg, 85 mm Hg or 75 mm Hg or combinations of said systolic blood pressure and diastolic blood pressure. An alternative characteristic of a healthy woman relates to the body mass index. Thus, in some embodiments of the invention, the woman has a body mass index in the range from about 16 to 35 in that the body mass index in older woman may be in the higher end of that range without being denoted obesive. Normally, to ensure low risk of hypertension and/or cardiovascular diseases, the body-mass index should be lower than 35. Therefore, the body-mass index of a woman is preferably in the range from about 18 to 32, even more preferably in the range from about 18 to 29, most preferably in the range from about 19 to 28, such as most preferably in the range from about 20 to 27.

Alternatively, the therapy and medicaments of the invention is used in women with an estimated risk of hypertension and/or cardiovascular disease above a specified level, wherein the risk is determined by measurement of risk factors used in conjunction with a person's age and sex. Thus, in one embodiment, the woman is susceptible to aldosterone-mediated diseases such as hypertension and/or cardiovascular diseases. A woman may be susceptible to cardiovascular diseases for a number of reasons such as because of hypertension, genetic disorders, race, diabetes, life-style, over-weight, smoking or food-intake. Thus, in some embodiments the woman can be hypertensive.

Moreover, a woman susceptible to hypertension and/or cardiovascular diseases may be characterised by having deficient endogenous levels of progesterone, such as a woman in peri-menopause or in post-menopause or a woman with irregular or abnormal bleeding, or such as a pregnant woman in risk of miscarriage. Thus, in some embodiments of the invention, the therapeutic methods or medicaments of the invention may be used to women having symptoms, diseases or disorders associated with deficient endogenous levels of progesterone, or to women in need of progesterone replacement therapy, such as a woman having irregular bleeding, abnormal bleeding, endometrioses and/or lack of ovulation.

Typically, the therapeutic methods and medicaments may also be applied to a healthy woman but nevertheless in the risk of developing hypertension and/or cardiovascular diseases. The woman may previously have been diagnosed as having had the clinical symptoms of hypertension and/or cardiovascular disease, irrespective of age or the values of risk factors. Therefore, in some embodiments of the invention, the woman having risk or even increased risk of hypertension and/or cardiovascular diseases is a woman with a systolic blood pressure greater than 130 mm Hg or a diastolic blood pressure greater than 85 mm Hg or both. Furthermore, the woman in risk may also be characterised by having activities ratio of plasma aldosterone (ng/dL) to plasma renin (ng/mL/hr) greater than about 30. Women with risk factors can promote the development of arteriosclerosis. Such risk factors are smoking, overweight, stress, genetic disposition, high blood pressure, disorders of lipid metabolism, lack of exercise and/or diabetes.

In particular embodiments of the invention, the therapeutic methods and medicaments are preferably directed to a peri-menopausal woman.

The term "peri-menopause" characterises the period immediately before and after the onset of menopause, and averages 4 years. Furthermore, the peri-menopause is characterised by abnormal and irregular bleeding. The peri-menopausal phase begins with the onset of climacteric symptoms when the cycle becomes irregular and ends one year after menopause. The end of peri-menopausal phase can be identified after a protracted period of time without bleeding.

That is to say that the peri-menopause is the period before entering menopause. Thus, in interesting embodiments of the invention the woman is in the age from about 40 to 55. The suitable age may also be from about 45 to 53, about 45 to 52, 46 to 52, 48 to 52 or from about 47 to 51 dependent on when the individual women experiences irregular bleeding or other symptoms on deficient endogenous levels of progestogen. However, the uses and therapeutic methods of the invention may not be limited to women of that age. Some women enter the menopause in a much younger age such as for example when they are in theirs thirties due to hypogonadal activities. Other women will enter the menopause upon hysterectomy.

As mentioned, low endogenous levels of progesterone are an indication of peri-menopause in a woman. However, post-menopausal women does also have low endogenous levels of progesterone or even lack of progesterone for which reason post-menopausal women may benefit from the additional prevention of development of hypertension and/or cardiovascular diseases upon administering a drug substance with progestational and anti-mineralocorticoid activity. As mentioned, the therapeutic methods and uses do not necessarily imply that the post-menopausal women are in estrogen replacement therapy.

The term "menopause" characterises the time in a woman's life when the ovaries stop producing estrogen. Menopause is usually recognised by the cessation of menstrual periods. Other symptoms of menopause include flashes, mood changes, and difficulty in sleeping and vaginal dryness. In the present context, the term menopause is to be understood as the last natural (ovary-induced) menstruation. If a woman is not menstruating because she has had a hysterectomy or endometrial ablation, other symptoms of menopause often alert her that menopause is starting. The average age of the onset of menopause is 51 years, and it most commonly occurs from age 47 to 53. The term "post-menopause" is the phase that begins at menopause and continues until death.

Accordingly, in some embodiments of the invention, the woman is a post-menopausal woman, e.g. a woman with deficient levels of endogenous estrogen. Although the women is post-menopausal it is preferred that said woman do not receive estrogen replacement therapy simultaneously with the therapy with aldosteronic progestins according to the invention.

That is to say that the therapeutic methods of the invention do not necessarily comprise concurrent administration of an estrogen. Likewise, medicaments and compositions of the invention does not necessarily further comprises an estrogen. In actual preferred embodiments, an estrogen is excluded. And in one aspect, the general methods and uses of this invention exclude the administration of effective amounts of DRSP and at least one estrogen to a hypertensive human female patient for purposes of effecting hormone replacement therapy and lowering blood pressure.

However, in some other embodiments, the therapeutic methods and uses are directed to the prevention of cardiovascular diseases and the simultaneous treatment of symptoms and diseases associated with deficient endogenous levels of estrogen in a woman, such as providing methods for the simultaneously prevention of cardiovascular diseases in a woman and treating symptoms of menopause as described above.

The deficient levels of estrogen may be caused by natural menopause, peri-menopause, post-menopause, hypogonadism, castration or by primary ovarian failure. The diseases, disorders and symptoms associated with deficient levels of estrogen may be any of or a mixture of the following conditions: hot flushes, sweating attacks, palpitations, sleep disorders, mood changes, nervousness, anxiety, poor memory, loss of confidence, loss of libido, poor concentration, diminished energy, diminished drive, irritability, urogenital atrophy, atrophy of the breasts, cardiovascular disease, changes in hair distribution, thickness of hair, changes in skin condition and/or osteoporosis.

The term "estrogen" includes both the natural 17β-estradiol and the semi-synthetic estrogen derivatives such as esters of natural estrogen and 17-alkylated estrogens. Semi-synthetic esters of natural estrogen include for example estradiol-17-β-enanthate, estradiol-17-β-valerate, estradiol-17-β-benzoate, estradiol-17-β-undecanoate, estradiol-16,17-hemisuccinate or estradiol-17-β-cypionate. Examples on 17-alkylated estrogens are Ethinylestradiol, Ethinylestradiol-3-isopropylsulphonate, quinestrol, mestranol or methyl estradiol. The term "estrogen" may also include a non-steroidal compound having estrogen activity, such as diethylstilbestrol, dienestrol, clomifen, chlorotrianesene or cyclofenil. Particular interesting estrogens are selected from the group consisting of estradiol, estradiol sulfamates, estradiol valerate, estradiol benzoate, estrone, and estrone sulfate or mixtures thereof, notably estradiol, estradiol valerate and estradiol benzoate. Most preferred are estradiol or esters thereof, particularly estradiol.

The dose of estrogen may vary from woman to woman, depending on the phase of her life (peri-menopausal or post-menopausal), endogenous levels of estrogen, the severity of the symptom(s), disorder or disease, the disorder, disease or symptom targeted, the use by the woman of other medicaments for other purposes, and other pharmacokinetic variables.

In other embodiments, the dose of estrogen is sufficient to treat hot flushes, sweating attacks, palpitations, sleep disorders, mood changes, nervousness, anxiety, poor memory, loss of confidence, loss of libido, poor concentration, diminished energy, diminished drive, irritability, urogenital atrophy, atrophy of the breasts, cardiovascular disease, changes in hair distribution, thickness of hair, changes in skin condition or for the prevention or management of osteoporosis.

In particular embodiments, the estrogen is estradiol and the amount of estradiol corresponds to a daily dose ranging from 0.1 to 5 mg, such as about 0.2 to 4.5, 0.5 to 4, 1 to 3, in particular 1, 2, or 3 mg.

In some embodiments of the invention, the woman is pregnant. In the event where the woman is pregnant the uses for preparation of a medicament and therapeutic methods of the invention comprises a drug substance exhibiting progestational and anti-mineralo-corticoid for the treatment of hypertension in a pregnant woman.

For all of the drug substances according to the invention, the dosage is selected to maximise the reduction of risk of hypertension and/or cardiovascular disease whilst minimising undesirable side effects. The dose will depend on the drug substance concerned.

The dosage of the drug substance according to the invention may be effective in reducing the risk of developing aldosterone-mediated diseases, such as hypertension and/or cardiovascular diseases, but not effective in treating symptoms and diseases associated with deficiencies in the endogenous levels of progesterone in a woman. That is to say that the dosage of the drug substance is below the effective dosage for treating irregular or abnormal bleeding in for example a perimenopausal woman. Thus in those embodiments, the dosage does not result in regular bleeding (cycle control) and/or normal bleeding in a woman or prevention of miscarriage in a pregnant woman. In such cases, it may be appropriate that the woman is in concurrent therapy with one or more alternative progestin(s) in dosages that will provide regular bleeding (cycle control), normal bleeding, treat endometrioses and/or treat other gynaecological disorders in a woman, or prevention of miscarriage in a pregnant woman. Without limitations, such alternative progestins may include those having low or substantially no aldosterone receptor blocker effect/anti-mineralocorticoid effect in comparison to Drospirenone. Such progestins are characterised by having low anti-mineralocorticoid effect and are equivalent to those mentioned above.

However, in some interesting aspects of the invention it is advantageous to use a dosage of the drug substance according to the invention that provides the prevention of hypertension and/or cardiovascular diseases and simultaneous treatment of symptoms and diseases associated with deficiencies in the endogenous levels of progesterone in a woman.

As mentioned, currently interesting embodiments of the invention include that the drug substance exhibiting progestational and anti-mineralocorticoid effect is drospirenone. In some embodiments of the invention, the dosage of drospirenone is effective in achieving regular and/or bleeding patterns in a woman, e.g. providing cycle control. Such doses may relate to drospirenone in a daily deliverable dose ranging from about 0.02 to 5 mg, preferably ranging from about 0.1 mg to 3 mg or from about 0.25 mg to 3 mg, such as 0.1, 0.25 mg, 0.5 mg, 1, 2 or 3 mg.

In other embodiments of the invention, the dosage of drospirenone would not implicate progestational activity but merely anti-mineralocorticoid effect. In such embodiments, drospirenone is in a daily deliverable dose ranging from about 0.02 to 5 mg, preferably in the range from about 0.1 to 5 mg, such as 0.1, 0.2, 0.5, 1, 2, 3, 4 or 5 mg. In some embodiments the dose is ranging from about 0.1 mg to 3 mg, more preferably in the range from about 0.1 to 2 mg, more preferably in the range from about 0.1 mg to 1.5 mg, more preferably in the range from 0.1 mg to 1.0 mg, such as 0.1-0.75 mg, 0.1-0,5 mg, 0.1-0.4 mg.

It may further be the understanding that such daily deliverable doses of Drospirenone or any other drug substance of the invention may be for oral administration or orally deliverable doses. In some embodiments, the Drospirenone is administered or in a composition formulated for being administered topically, such as to skin or to rectal or vaginal mucosa so as the Drospirenone is absorbed systemically into the blood circulation.

In some embodiments of the invention, drospirenone can be administered in dosages which are effective for preventing myocardial fibrosis but insufficient to substantially increase sodium excretion or substantially reduce potassium retention, reduce hypertension, reduce water retention, affect blood pressure, and/or lower arterial blood pressure. Hence, the daily or monthly deliverable dose of drospirenone may not significantly alter the blood pressure but may still be able to antagonise the cardiac effects of aldosterone.

The drug substance according to this invention may be delivered daily to the blood plasma, the mineralocorticoid receptor and/or the progestational receptor for a number of days within each cycle of 21 to 35 days, preferably within each cycle of 28 days. Cycle is intended to mean a period of time that is repeated for every 21 to 35 days. In some embodiments the delivery of the drug substance may be for at least 5 days up to 35 days. In other embodiments the drug substance is delivered for at least 10 days, such as 12 days, such as 15 days, such as 20 days, such as 21, 22, 23, 24, 25, 26, 27, or 28 days within each cycle of 21 to 35 days, preferably 28 days. In some embodiments the delivery is in interrupted manner, which means that the drug substance is delivered for a period of time, which is followed by a period with no drug substance delivered, which is then followed by a period with delivery of the drug substance. Also, it means that no drug substance is delivered for a period of time, followed by delivery of drug substance, followed by no delivery of drug substance. This cycling of delivery of a drug substance may be repeated 1 to 10 times within a cycle of 21 to 35 days. That is to say that each delivery of drug substance may for example be conducted for 1, 3, 7, 14 or 21 days. The length of the period with delivery of drug substance may be similar, minor or greater than the period with no delivery. In some embodiments, the drug substance exhibiting progestational and anti-mineralocorticoid activity is administered sequentially, which relates to an interrupted manner.

In other embodiments, the drug substance of the invention, such as a drug substance exhibiting progestational and anti-mineralocorticoid activity is administered continuously within a treatment cycle of 21 to 35 days.

The dose delivered by the drug substance may vary throughout the period of 21 to 35 days or it may be the same. Thus, in some embodiments, the dose delivered varies throughout the period of 21 to 35 days. For example, the dose may be lower in the first half, such as within the first 10 days, of the period of 21 to 35 days than in the second half, such as the last 10 days, of the period of 21 to 35 days. Conversely, it may also be suitable to use a higher dose in the first half, such as within the first 10 days, of the period of 21 to 35 days than in the second half, such as the last 10 days of the period of 21 to 35 days.

The composition according to the invention may be formulated in any suitable manner. In suitable embodiments of the invention, the composition is formulated, according to the person skilled in the art, as a dosage unit for oral or topical administration. Preferable, the composition is formulated for oral delivery of the active drug substance.

The dosage unit formulated for oral administration may be a solid, semisolid or fluid formulation. The solid dosage units may be selected from the group consisting of uncoated tablets, modified-release tablets, gastro-resistant tablets, orodispersible tablets, effervescent tablets, chewable tablets, soft capsules, hard capsules, modified-release capsules, gastro-resistant capsules, uncoated granules, effervescent granules, coated granules, gastro-resistant granules, modified-release granules, and powders for oral administration; and the fluids are selected from the group consisting of solutions, suspensions or emulsions.

The dosage units for topical administration may be selected from the group consisting of creams, gels, emulsions, suspensions, lotions, suppositories, enemas, pessaries, vaginal capsules, vaginal tablets, pads, sponges, plasters and transdermal delivery systems. The dosage units for parenteral administration may be selected from the group consisting of solutions, suspensions, emulsions, gels, implantation tablets or implants.

Administration of dosage units comprising combinations of active drug substances such as a selective aldosterone antagonist and a progestin with low or substantially no anti-mineralocorticoid effect can occur concomitantly or independently. That is to say that the combination is administered in a single dosage form or as more than one dosage form such as one drug substance administered as a solid and the other drug substance as a fluid. Similarly, one drug substance may be formulated for oral administration whilst the other is formulated for transdermal or subcutaneous administration. In a preferred embodiment, both drug substances are administered as solids formulated for oral administration.

Moreover, an interesting embodiment of the invention comprises a dosage unit wherein the drospirenone is in micronized form or in the form of a cyclodextrin inclusion complex.

The dosage unit of the present invention comprises carriers or excipients, which may act to promote dissolution of both active substances. Examples of such carriers and excipients include substances that are readily soluble in water such as cellulose derivatives, carboxymethyl cellulose, hydroxypropyl cellulose, hydroxypropyl methyl cellulose, gelled starch, gelatin or polyvinylpyrrolidone. In particular, it is anticipated that polyvinylpyrrolidone might be particularly helpful to promote dissolution.

The term "pharmaceutically acceptable carriers and excipients" is intended to mean substances, which are substantially harmless to the individual to which the dosage unit will be administered. Such an excipient normally fulfils the requirements given by the national drug agencies. Official pharmacopeias such as the British Pharmacopeia, the United States of America Pharmacopeia and the European Pharmacopeia set standards for well-known pharmaceutically acceptable excipients.

Suitable pharmaceutically acceptable excipients according to the invention include all kinds that may be used for solid, semi-solid and fluid dosage units.

EXAMPLES

Example 1

Determination of the preventive effect on hypertension and/or cardiovascular diseases in women.

Design

Cohort study of users of hormone replacement therapy with Drospirenone and optionally an estrogen, such as estradiol.

Study Participants

The cohort study will include at least 1000, preferably at least 5000, 10000, 20000 or 30000 women enlisted by physicians. The eligibility of participating women will be determined by the prescribing physician following usual indication for continuous-combined hormone replacement. The chief goal is to accrue per- and/or post-menopausal women. Inclusion criterion will be the decision of the physician to prescribe HRT. This definition supports the aim of the active surveillance study to reflect real-life conditions.

Information Gathered

Exposure data: Exposure is defined—for this surveillance study—as use of therapy with Drospirenone, preferably as monotherapy without no further medication with an estrogen. Alternative progestins with same pharmacological profile as Drospirenone may also be defined as "exposed".

Confounding factors: Factors to be considered and adjusted including the following: age, smoking, hypertension, increased blood lipids, diabetes mellitus, body mass index, cardiovascular diseases (angina pectoris, myocardial infarction, stroke/TIA, venous thromboembolism), family history of premature cardiovascular events (MI and stroke), and liver and kidney diseases. In the analyses, other potential confounders may come to light and they will be adjusted for as appropriate.

Outcomes: The outcomes of particular interest are (with an estimated average incidence rate in women of the age group 40-65 years): cardiovascular mortality, myocardial infarction morbidity, morbidity of arrhythmias, and venous thromboembolism. The relevant information will be gathered with a short Self-Administered Questionnaire to be completed by the participating women (with contact to their physicians when necessary). The Baseline Questionnaire contains questions related to the state of health, risk factors (medical history) and confounders, including drug use (Table 1). The follow-up assessment of the combined cohort will be done after 6, 12 months, and thereafter every year using a questionnaire mailed to the cohort members.

TABLE 1

Summary of the content of the two questionnaires: the baseline form and the form that will be completed at least after 6, 12, 24, and 36 months after the baseline inquiry

| Baseline Questionnaire | Follow-up Questionnaire |
|---|---|
| ID-number; birthday; date of last menstrual bleeding; artificial menopause (operation); parity, births (number), stillbirths, abortions; OC-use, age at start and stop, duration of OC-use; ever HRT, | ID-number; occurrence of new conditions after last contact such as high blood pressure, hypertension, high cholesterol, diabetes, myocardial infarction, arrhythmias (confirmed by |

TABLE 1-continued

Summary of the content of the two questionnaires: the baseline form and the form that will be completed at least after 6, 12, 24, and 36 months after the baseline inquiry

| Baseline Questionnaire | Follow-up Questionnaire |
|---|---|
| how many different brands, duration of HRT, how many switches among brands, date of stopping HRT, problems during HRT use, name of last brand, name of current prescription; smoking status (current, ex-, never smoker, number cigarettes now and before stopping, date of stopping; history of hypertension, high cholesterol, diabetes mellitus, myocardial infarction, arrhythmias (confirmed by ECG), stroke, pulmonary embolism, deep venous thrombosis, varicose veins, abnormal liver test, abnormal kidney function, osteoporosis, hip fracture, spine fracture, any cancer, any operation, other health problems (specify); family history of myocardial infarction or stroke before age 50; regular use of medicaments (specify); recent blood pressure reading; height, weight, recent loss in weight. | ECG), stroke, venous thromboembolism; abnormal liver tests; abnormal kidney function, hip fracture, spine fracture, other fractures, any cancer, any operation, other health problems (specify); all brand names of HRTs used since the last contact (with dates, and reason for switching); regular use of medicaments (specify); changes of smoking status; weight, height; other relevant information; personal changes; name of treating physician, hospital to enable contact (in case that an AE/SAE occurred). |

If serious adverse events (SAEs) are reported by the women, the investigators will discuss these events with the relevant professionals and record the information. In case of SAEs possibly related to HRT use, a SAE reporting form will be completed in correspondence with the treating physician—irrespective of whether or not the physician has already spontaneously reported the event through official channels in the respective country. Necessary steps will be taken to facilitate rapid reporting in case when there are cases of unexpected SAEs. The respective manufacturers of the HRT products will be informed about SAEs that occurred.

Data Handling

The questionnaire will first be checked manually for completeness and consistency at the coordinating centre. In case of missing data, contradictions, questions, or obvious errors the participants will be contacted for clarification. After completion of the manual checks, the forms will be entered into a computer data bank designed to meet the specific needs of a long-term cohort study.

Non-respondents will be sent a second, and in case of a second non-response, a third mailing. To further maximise follow-up after baseline survey, the women will be asked at every contact to announce any personal changes, e.g. telephone number. In case a woman reports any of a specified list of medical outcomes, a follow-up form will be sent out to request consent to inspect the medical records. Information on the name of the relevant physician, the hospital, etc. will be recorded in order to gain access to the records.

Study Size Estimation

To detect a increased risk of certain outcomes associated with the present therapy with 95% probability and a power of 80%, the required number of women-years of the combined cohort should have the following magnitude for a detectable risk of 3.0: cardiovascular mortality 18.000, myocardial infarction 12.000, arrhythmias 9.000, and venous thromboembolism 20.000 women years. For the time being, it is a reasonable assumption that statistical power will be adequate to determine the preventive effect on hypertension and/or cardiovascular event. Even if an OR of 2.0 should be detected, it is assumed that the data would be reasonable robust.

Evaluation

It would not be possible to confine the study to non-predisposed women, since an important objective in this study will be to determine risk according to the baseline risk status. It will be important to control confounding and to evaluate possible effect modification from various sources. Reported serious adverse events will be validated against medical records. The ascertaining of (sudden) deaths will be accomplished by cross-reference to relevant Death Registries.

Interim Evaluations

At least twice annually descriptive statistics made including the data on the number of women enrolled in the various user cohorts, the observed duration and type of continuous-combined HRT use, the number and nature of serious AEs for all users of the new continuous-combined HRT and the other continuous-combined HRT combined but separately for starters and switchers, and—if relevant—for certain formulations or specific events (e.g., sudden death, cardiovascular events, or other major events), provided that sufficient numbers have been obtained or the nature of the events is serious, unexpected, or relevant for the study objectives.

Any adverse events mentioned in the follow-up questionnaires or received as separate.

Final Analysis

In the interpretation of the findings, the greatest emphasis will be on relative risk estimates of high magnitude. Relative risk estimates under 3.0 will be considered as inconclusive, because it is methodologically impossible to distinguish between causation, bias, and confounding. In the interpretation of the impact of the results on public health (safety), the main emphasis will be on the absolute risk estimates.

All analyses will make allowance for confounding by methods that will include multivariate techniques such as Cox regression, stratification by the Mantel-Haensel procedure, and exclusion of women with any of a list of specific confounders at baseline. Some confounders that can be quantified with precision (e.g., smoking status; obesity) will not be excluded, but controlled in the analysis.

Example 2

A composition comprising Drospirenone may be manufactured in the following manner:

| Tablet cores of the following composition | |
|---|---|
| Drospirenone (preferably micronised) | 3.00 mg |
| lactose monohydrate | 45.2 mg |
| corn starch | 14.40 mg |
| modified starch | 9.60 mg |
| polyvinylpyrrolidone 25,000 | 4.00 mg |
| magnesium stearate | 0.80 mg | are prepared by charging a fluidised bed granulator with corn starch, modified starch, drospirenone, lactose monohydrate and activating the fluidised bed. An aqueous solution of polyvinylpyrrolidone 25,000 in purified water is sprayed continuously onto the fluidised bed while drying by heating the air stream of the fluidised bed. At the end of the process magnesium stearate is sucked into the granulator and mixed with the granules by maintaining the fluidised bed. The resulting granulate is pressed into tablet cores by compression using a rotary tablet press.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. Also, any preceding examples can be repeated with similar success by substituting the generically or specifically described reactants and/or operating conditions of this invention for those used in such examples.

Throughout the specification and claims, all temperatures are set forth uncorrected in degrees Celsius and, all parts and percentages are by weight, unless otherwise indicated.

The entire disclosure of all applications, patents and publications, cited herein and of corresponding U.S. application Ser. No. 10/287,780, filed Nov. 5, 2002, now Provisional Application Ser. No. 60/608,961, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for treating hypertension in a woman comprising administering drospirenone as the sole therapeutically active agent to said woman, and wherein said drospirenone is administered daily in a solid unit dosage form containing a dose of drospirenone of 2, 2.5, or 3 mg.

2. The method of claim 1, wherein said woman is perimenopausal

3. The method of claim 1, wherein said woman is postmenopausal.

4. The method of claim 1, wherein 2.5 mg of drospirenone is administered to said woman.

5. The method of claim 1, wherein 2 mg of drospirenone is administered to said woman.

6. The method of claim 1, wherein said drospirenone is micronized drospirenone.

7. The method of claim 6, wherein said unit dosage form contains a dose of micronized drospirenone of 2 mg.

8. The method of claim 1, wherein said unit dosage form contains a dose of micronized drospirenone of 3 mg.

9. The method of claim 1, wherein said unit dosage form contains a dose of drospirenone of 3 mg.

* * * * *